US007837996B2

(12) United States Patent
Drakenberg et al.

(10) Patent No.: US 7,837,996 B2
(45) Date of Patent: Nov. 23, 2010

(54) MATERIALS AND METHODS FOR TREATMENT OF HEPATITIS C

(75) Inventors: Katarina Drakenberg, Lindingo (SE); Mats A. A. Persson, Stockholm (SE)

(73) Assignee: Molecules of Man AB, Bromma (SE)

( * ) Notice: Subject to any disclaimer, the term of this patent is extended or adjusted under 35 U.S.C. 154(b) by 369 days.

(21) Appl. No.: 11/774,059

(22) Filed: Jul. 6, 2007

(65) Prior Publication Data
US 2009/0162373 A1  Jun. 25, 2009

Related U.S. Application Data

(62) Division of application No. 10/466,242, filed as application No. PCT/SE02/00044 on Jan. 14, 2002, now Pat. No. 7,250,166.

(60) Provisional application No. 60/260,889, filed on Jan. 12, 2001.

(51) Int. Cl.
A61K 39/42 (2006.01)
A61K 39/29 (2006.01)
(52) U.S. Cl. ................ 424/147.1; 424/228.1
(58) Field of Classification Search ............ None
See application file for complete search history.

(56) References Cited

U.S. PATENT DOCUMENTS

| 6,150,134 | A | 11/2000 | Maertens | |
|---|---|---|---|---|
| 6,538,114 | B1 | 3/2003 | Persson | |
| 6,692,908 | B1 | 2/2004 | Foung | |
| 6,747,136 | B2 | 6/2004 | Persson | |
| 7,250,166 | B2 * | 7/2007 | Drakenberg et al. | 424/149.1 |
| 2003/0180284 | A1 | 9/2003 | Foung | |

FOREIGN PATENT DOCUMENTS

| EP | 0947525 | 10/1999 |
|---|---|---|
| WO | 97/40176 | 10/1997 |
| WO | 00/26418 | 5/2000 |
| WO | 02/057314 | 7/2002 |
| WO | 2004/005316 | 1/2004 |

OTHER PUBLICATIONS

Saadeh et al. Cleveland Clinic Journal of Medicine, 2004, vol. 71, supplement 3, pp. S3-S7.
McHutchinson et al. Hepatology, 2002, 36 :S245-252.
Berzofsky et al. The Journal of Clinical Investigation, 2004, 114(4):450-462.
Colman, P.M. Effects of amino acid sequence changes on antibody-antigen interactions, Research Immunology, Jan. 1994, vol. 145, pp. 33-36.
Bartosch, B. et al. "Infectious Hepatitis C Virus Pseudo-particles Containing Functional E1-E2 Envelope Protein Complexes"; The Journal of Experimental Medicine, 197(5): 633-642 (2003).
Hsu, M. et al. "Hepatitis C virus glycoproteins mediate pH-dependent cell entry of pseudotyped retroviral particles"; PNAS, 100(12): 7271-7276 (2003).
De Beeck, A.O. et al. "Characterization of Functional Hepatitis C. Virus Envelope Glycoproteins"; Journal of Virology, 78(6): 2994-3002 (2004).
Logvinoff, C. et al. "Neutralizing antibody response during acute and chronic hepatitis C virus infection"; PNAS, 101 (27): 10149-10154 (2004).
Keck, Z. et al. "Human Monoclonal Antibody to Hepatitis C Virus E1 Glycoprotein That Blocks Virus Attachment and Viral Infectivity"; Journal of Virology, 78(13): 7257-7263 (2004).
Burioni, R. et al. "Cross-reactive pseudovirus-neutralizing anti-envelope antibodies coexist with antibodies devoid of such activity in persistent hepatitis C virus infection"; Virology, 327: 242-248 (2004).
Ludwig, I.S. et al. "Hepatitis C Virus Targets DC-SIGN and L-SIGN to Escape Lysosomal Degradation"; Journal of Virology, 78(15): 8322-8332 (2004).
McKeating, J.A. et al. "Diverse Hepatitis C Virus Glycoproteins Mediate Viral Infection in a CD81-Dependent Manner"; Journal of Virology, 78(16): 8496-8505 (2004).
Taguchi, H. et al. "Antibody light chain-catalyzed hydrolysis of a hepatitis C virus peptide"; Bioorganic & Medicinal Chemistry Letters, 14: 4529-4532 (2004).
Persson, M.A., et al., "Generation of diverse high-affinity human monoclonal antibodies by repertoire cloning," PNAS, 88:2432-2436 (Mar. 1991).
Database GENESEQP library, accession No. AAB52199, Feb. 22, 2001, retrieved from EBI.
Database GENESEQP library, accession No. AAG63656, Oct. 29, 2001, retrieved from EBI.
Database GENESEQP library, accession No. AAW13922, May 15, 1997, retrieved from EBI.
Database GENESEQP library, accession No. AAG63655, Oct. 29, 2001, retrieved from EBI.
Allander, T., et al., "Recombinant human monoclonal antibodies different conformational epitopes of the E2 envelope glycoprotein of hepatitis C virus that inhibit its interaction with CD81," J. Gen. Virol. 81(pt. 10):2451-9, (Oct. 2000).

* cited by examiner

*Primary Examiner*—Stacy B Chen
(74) *Attorney, Agent, or Firm*—Kathleen D. Rigaut; Dann, Dorfman, Herrell & Skillman

(57) ABSTRACT

The present invention relates to materials and methods for treatment of hepatitis C. More closely, the invention relates to human monoclonal antibodies against HCV E1 antigen, to a reagent comprising such antibodies, and to vaccine compositions comprising such antibodies. Furthermore, the invention relates to a method of treating or preventing HCV infection by administration of a vaccine composition comprising the monoclonal antibodies of the invention.

4 Claims, No Drawings

SEQUENCE LISTING

```
<160> NUMBER OF SEQ ID NOS: 56

<210> SEQ ID NO 1
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: Clone 13 VH

<400> SEQUENCE: 1

Ala Glu Val Gln Leu Glu Ser Gly Gly Gly Leu Val Gln Pro Gly
1               5                   10                  15

Arg Ser Leu Arg Leu Ser Cys Ala Ala Ser Gly Phe Thr Phe Asp Asp
                20                  25                  30

Tyr Gly Met His Trp Val Arg Gln Ala Pro Gly Lys Gly Leu Glu Trp
            35                  40                  45

Val Ser Gly Leu Ser Trp Asn Ser Asp Asn Ile Gly Tyr Ala Asp Ser
        50                  55                  60

Val Lys Gly Arg Phe Thr Ile Ser Arg Asp Asn Ala Lys Asn Ser Leu
65                  70                  75                  80

Tyr Leu Gln Met Asn Ser Leu Lys Ile Glu Asp Thr Ala Phe Tyr Tyr
                85                  90                  95

Cys Ala Lys Ala Pro Arg Thr Leu Arg Phe Leu Glu Trp His Asn Val
            100                 105                 110

Tyr Phe Asp Leu Trp Gly Arg Gly Thr Leu Val Thr Val Ser Ser
        115                 120                 125

<210> SEQ ID NO 2
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: Clone 13 VK

<400> SEQUENCE: 2

Ala Glu Leu Thr Gln Ser Pro Asp Ser Leu Ala Val Ser Leu Gly Glu
1               5                   10                  15

Arg Ala Thr Ile Asn Cys Lys Ser Ser Gln Ser Val Leu Tyr Ser Ser
                20                  25                  30

His Asn Lys Asn Tyr Leu Ala Trp Tyr Gln Gln Lys Pro Gly Gln Pro
            35                  40                  45

Pro Lys Leu Leu Ile Tyr Trp Ala Ser Thr Arg Glu Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Phe Ser Thr Pro Leu Thr Phe Gly Gly Gly Thr Lys Val Glu Ile Lys
            100                 105                 110
```

<210> SEQ ID NO 3
<211> LENGTH: 133
<212> TYPE: PRT
<213> ORGANISM: Homo sapiens
<220> FEATURE:
<221> NAME/KEY: PEPTIDE
<222> LOCATION: (1)..(133)
<223> OTHER INFORMATION: Clone 98 VH

<400> SEQUENCE: 3

Ala Glu Val Gln Leu Leu Glu Gln Ser Gly Ala Glu Val Lys Lys Pro
1               5                   10                  15

Gly Glu Ser Leu Arg Ile Ser Cys Arg Gly Ser Gly Tyr Ser Phe Pro
            20                  25                  30

Asn Tyr Trp Val Ser Trp Val Arg Gln Met Pro Gly Lys Gly Leu Glu
        35                  40                  45

Trp Met Gly Lys Ile Asp Pro Ser Asp Ser Glu Thr Asn Tyr Ser Pro
50                  55                  60

Ser Phe Gln Gly His Val Thr Ile Ser Ala Asp Lys Ser Leu Ser Ile
65                  70                  75                  80

Ala Tyr Leu Gln Trp Asn Ser Leu Lys Ala Ser Asp Thr Ala Met Tyr
                85                  90                  95

His Cys Ala Arg His Lys Arg Gly Ala Pro Thr Tyr Lys Asp Ile Leu
            100                 105                 110

Thr Gly Tyr Tyr Val Asp Gly Met Asp Val Trp Gly Gln Gly Thr Thr
        115                 120                 125

Asp Thr Val Ser Ser
        130

<210> SEQ ID NO 4
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 98 VK

<400> SEQUENCE: 4

Ala Glu Leu Thr Gln Ser Pro Ser Ser Leu Ser Ala Ser Val Gly Asp
1               5                   10                  15

Arg Val Thr Ile Thr Cys Gln Ala Ser Pro Asp Ile Ser Asn Tyr Leu
            20                  25                  30

Asn Trp Tyr Gln Gln Lys Pro Gly Lys Ala Pro Asn Leu Leu Ile Tyr
        35                  40                  45

Gly Ala Ser Ser Leu Gln Arg Gly Val Pro Ser Arg Leu Ser Gly Ser
    50                  55                  60

Gly Ser Gly Thr Asp Phe Thr Leu Thr Ile Asp Ser Leu Gln Pro Glu
65                  70                  75                  80

Asp Phe Ala Thr Tyr Tyr Cys Gln Gln Ser Tyr Gly Ser Pro His Thr
                85                  90                  95

Phe Gly Gln Gly Thr Lys Val Glu Ile Lys
            100                 105

<210> SEQ ID NO 5
<211> LENGTH: 125
<212> TYPE: PRT
<213> ORGANISM: Homo sapiens
<220> FEATURE:

```
<221> NAME/KEY: PEPTIDE
<222> LOCATION: (1)..(125)
<223> OTHER INFORMATION: Clone 1:4 VH

<400> SEQUENCE: 5

Ala Glu Val Gln Leu Leu Glu Ser Gly Pro Gly Leu Val Lys Pro Ser
1               5                   10                  15

Glu Thr Leu Ser Leu Thr Cys Thr Val Ser Asn Gly Ser Met Ser Asn
            20                  25                  30

Tyr Cys Trp Ser Trp Ile Arg Gln Ser Pro Gly Lys Gly Leu Glu Trp
        35                  40                  45

Ile Gly Tyr Ile Tyr Tyr Ser Gly Ser Thr Ser Tyr Asn Pro Ser Leu
50                  55                  60

Arg Ser Arg Val Ala Leu Leu Val Asp Thr Ser Lys Asn Gln Phe Ser
65                  70                  75                  80

Leu Lys Leu Thr Ser Val Thr Thr Ala Asp Thr Ala Val Tyr Tyr Cys
                85                  90                  95

Ala Arg Asp Leu Ser Ala Arg Gly Gly Thr Arg Asn Arg Asp Ala Leu
            100                 105                 110

Asp Val Trp Gly Gln Gly Thr Gln Val Thr Val Ser Ala
        115                 120                 125

<210> SEQ ID NO 6
<211> LENGTH: 107
<212> TYPE: PRT
<213> ORGANISM: Homo sapiens
<220> FEATURE:
<221> NAME/KEY: PEPTIDE
<222> LOCATION: (1)..(107)
<223> OTHER INFORMATION: Clone 1:4 VK

<400> SEQUENCE: 6

Ala Glu Leu Thr Gln Ser Pro Ala Thr Leu Ser Val Ser Pro Gly Glu
1               5                   10                  15

Arg Ala Thr Leu Ser Cys Arg Ala Ser Gln Ser Val Asn Ser Asn Leu
            20                  25                  30

Ala Trp Tyr Gln Gln Lys Pro Gly Gln Ala Pro Ser Leu Leu Ile Tyr
        35                  40                  45

Gly Ala Ser Thr Arg Ala Thr Gly Ile Pro Ala Arg Phe Ser Gly Ser
50                  55                  60

Gly Ser Gly Thr Glu Leu Thr Leu Thr Ile Ser Ser Leu Gln Ser Glu
65                  70                  75                  80

Asp Phe Ala Val Tyr Tyr Cys Gln Gln Tyr Lys Asn Trp Pro Pro Trp
                85                  90                  95

Thr Phe Gly Gln Gly Thr Lys Val Glu Ile Lys
            100                 105

<210> SEQ ID NO 7
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: Clone 1:8 VH

<400> SEQUENCE: 7

Ala Glu Val Gln Leu Leu Glu Ser Gly Gly Gly Leu Val Glu Pro Gly
1               5                   10                  15

Arg Ser Leu Arg Leu Ser Cys Ala Ala Ser Gly Phe Asn Phe Gly Asp
```

```
                    20                  25                  30
Tyr Ala Ile His Trp Val Arg Gln Gly Pro Gly Lys Gly Leu Glu Trp
            35                  40                  45
Val Ala Gly Ile Ser Trp Asn Ser Gly Ser Ile Gly Tyr Ala Asp Ser
 50                  55                  60
Val Lys Gly Arg Phe Ile Ile Ser Arg Asp Asn Ala Lys Lys Thr Leu
 65                  70                  75                  80
Phe Leu Gln Met Asn Thr Leu Arg Thr Glu Asp Thr Ala Leu Tyr Tyr
                85                  90                  95
Cys Val Lys Glu Thr Gly Ala Gly Val Ala Gly Ser Gly Ala Tyr
                100                 105                 110
Tyr Phe His Asn Trp Gly Gln Gly Thr Leu Val Thr Val Ser Ser
            115                 120                 125
```

<210> SEQ ID NO 8
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 1:8 VK

<400> SEQUENCE: 8

```
Ala Glu Leu Thr Gln Ser Pro Ser Ser Leu Ser Ala Ser Ile Gly Asp
 1               5                  10                  15
Arg Val Thr Ile Thr Cys Arg Ala Ser Gln Gly Ile Ser Asn Tyr Val
                20                  25                  30
Ala Trp Tyr Gln Gln Arg Pro Gly Lys Val Pro Lys Leu Leu Ile Phe
            35                  40                  45
Gly Ala Ser Ala Leu His Ser Gly Val Pro Ser Arg Phe Ser Gly Ser
 50                  55                  60
Gly Ser Gly Thr Asp Phe Thr Leu Thr Ile Thr Ser Leu Gln Pro Glu
 65                  70                  75                  80
Asp Val Ala Thr Tyr Tyr Cys Gln Lys Tyr Arg Ser Ala Pro Leu Thr
                85                  90                  95
Phe Gly Pro Gly Thr Arg Val Asp Leu Lys
                100                 105
```

<210> SEQ ID NO 9
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Clone 1:9 VH

<400> SEQUENCE: 9

```
Ala Glu Val Gln Leu Leu Glu Ser Gly Pro Gly Leu Val Lys Pro Ser
 1               5                  10                  15
Glu Thr Leu Ser Leu Thr Cys Thr Val Ser Gly Asn Ser Ile Ser Ser
                20                  25                  30
Gly Tyr Tyr Trp Val Trp Phe Arg Gln Ser Pro Gly Lys Gly Leu Glu
            35                  40                  45
Trp Ile Ala Ser Ile Tyr His Ser Gly Ser Thr Tyr Tyr Asn Pro Ser
 50                  55                  60
Leu Arg Ser Arg Val Ser Ile Ser Val Asp Thr Ser Lys Lys Gln Phe
 65                  70                  75                  80
```

-continued

```
Ser Leu Lys Leu Ser Ser Val Thr Ala Ala Asp Thr Ala Val Tyr Tyr
                85                  90                  95

Cys Ala Arg Asp Ser Ala Lys Thr Thr Arg Tyr Phe Val His Trp Gly
            100                 105                 110

Gln Gly Thr Leu Val Thr Val Ser Ser
        115                 120

<210> SEQ ID NO 10
<211> LENGTH: 109
<212> TYPE: PRT
<213> ORGANISM: Homo sapiens
<220> FEATURE:
<221> NAME/KEY: PEPTIDE
<222> LOCATION: (1)..(109)
<223> OTHER INFORMATION: Clone 1:9 VK

<400> SEQUENCE: 10

Ala Glu Leu Thr Gln Ser Pro Gly Thr Leu Ser Leu Ser Pro Gly Glu
1               5                   10                  15

Arg Ala Thr Leu Ser Cys Arg Ala Ser Gln Ser Val Ser Ser Ser Tyr
            20                  25                  30

Leu Ala Trp Tyr Gln Gln Lys Ala Gly Gln Ala Pro Arg Leu Leu Ile
        35                  40                  45

Tyr Gly Ala Ser Arg Arg Ala Thr Gly Ile Pro Val Arg Phe Ser Gly
    50                  55                  60

Ser Gly Ser Gly Ala Glu Phe Thr Leu Thr Ile Ser Ser Leu Gln Ser
65                  70                  75                  80

Glu Asp Ser Ala Val Tyr Tyr Cys Gln His Tyr His Asn Trp Pro Ala
                85                  90                  95

Met Tyr Thr Phe Gly Gln Gly Thr Lys Leu Glu Ile Lys
            100                 105

<210> SEQ ID NO 11
<211> LENGTH: 132
<212> TYPE: PRT
<213> ORGANISM: Homo sapiens
<220> FEATURE:
<221> NAME/KEY: PEPTIDE
<222> LOCATION: (1)..(132)
<223> OTHER INFORMATION: Clone 1:10 VH

<400> SEQUENCE: 11

Ala Glu Val Gln Leu Leu Glu Ser Gly Ala Glu Val Lys Lys Pro Gly
1               5                   10                  15

Glu Ser Leu Arg Ile Ser Cys Arg Gly Ser Gly Tyr Ser Phe Pro Asn
            20                  25                  30

Tyr Trp Val Ser Trp Val Arg Gln Met Pro Gly Lys Gly Leu Glu Trp
        35                  40                  45

Met Gly Lys Ile Asp Pro Ser Asp Ser Glu Thr Asn Tyr Ser Pro Ser
    50                  55                  60

Phe Gln Gly His Val Thr Ile Ser Ala Asp Lys Ser Leu Ser Ile Ala
65                  70                  75                  80

Tyr Leu Gln Trp Asn Ser Leu Lys Ala Ser Asp Thr Ala Met Tyr Tyr
                85                  90                  95

Cys Ala Arg His Lys Arg Gly Ala Pro Thr Tyr Lys Asp Ile Leu Thr
            100                 105                 110

Gly Tyr Tyr Val Asp Gly Met Asp Val Trp Gly Gln Gly Thr Thr Val
        115                 120                 125
```

```
Thr Val Ser Ser
    130

<210> SEQ ID NO 12
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: Clone 1:10 VK

<400> SEQUENCE: 12

Ala Glu Leu Thr Gln Ser Pro Asp Ser Leu Ala Met Ser Leu Gly Glu
1               5                   10                  15

Arg Ala Ser Ile Asn Cys Lys Ser Ser Arg Ser Leu Leu Tyr Ser Ser
                20                  25                  30

Asn Asn Lys Asn Tyr Leu Ala Trp Tyr Gln Gln Lys Ser Gly His Pro
            35                  40                  45

Pro Lys Leu Leu Ile Tyr Trp Ala Ser Thr Arg Glu Ser Gly Val Pro
    50                  55                  60

Asp Arg Phe Asn Gly Ser Gly Ser Gly Thr Asp Phe Thr Leu Thr Ile
65                  70                  75                  80

Ser Ser Leu Gln Ala Glu Asp Val Ala Val Tyr Phe Cys Gln Gln Tyr
                85                  90                  95

Tyr Ser Ser Pro Leu Thr Phe Gly Gly Gly Thr Lys Val Glu Ile Lys
            100                 105                 110

<210> SEQ ID NO 13
<211> LENGTH: 125
<212> TYPE: PRT
<213> ORGANISM: Homo sapiens
<220> FEATURE:
<221> NAME/KEY: PEPTIDE
<222> LOCATION: (1)..(125)
<223> OTHER INFORMATION: Clone 4:6 VH

<400> SEQUENCE: 13

Ala Glu Val Gln Leu Leu Glu Gln Ser Gly Ala Glu Val Lys Lys Pro
1               5                   10                  15

Gly Ala Ser Val Lys Val Ser Cys Lys Ala Ser Gly Tyr Thr Phe Thr
                20                  25                  30

Lys Tyr Tyr Leu His Trp Val Arg Gln Ala Pro Gly Gln Gly Leu Glu
            35                  40                  45

Trp Met Gly Phe Ile Asn Pro Ser Gly Gly Ser Thr Ser Ser Ala Gln
    50                  55                  60

Lys Phe Gln Gly Arg Ile Ser Met Thr Arg Asp Thr Ser Thr Thr Thr
65                  70                  75                  80

Val Tyr Met Glu Val Asn Ser Val Thr Ser Glu Asp Thr Ala Val Tyr
                85                  90                  95

Tyr Cys Ala Arg Val Gly Arg Leu Gly Val Gly Ala Thr Gly Ala Phe
            100                 105                 110

Asp Leu Trp Gly Gln Gly Thr Met Val Thr Val Ser Ser
    115                 120                 125

<210> SEQ ID NO 14
<211> LENGTH: 107
<212> TYPE: PRT
<213> ORGANISM: Homo sapiens
<220> FEATURE:
<221> NAME/KEY: PEPTIDE
```

<222> LOCATION: (1)..(107)
<223> OTHER INFORMATION: Clone 4:6 VK

<400> SEQUENCE: 14

Ala Glu Leu Thr Gln Ser Pro Ser Ser Leu Ser Ala Ser Val Gly Asp
1               5                   10                  15

Arg Val Thr Ile Thr Cys Gln Ala Ser Gln Asp Ile Asn Tyr Ser Leu
            20                  25                  30

Asn Trp Tyr Gln Gln Lys Pro Gly Lys Pro Lys Leu Leu Ile Tyr
        35                  40                  45

Tyr Ala Ser His Ser Asp Thr Gly Val Pro Ser Arg Phe Ser Gly Gly
    50                  55                  60

Gly Ser Gly Thr Arg Phe Thr Leu Thr Ile Tyr Ser Leu Gln Pro Glu
65                  70                  75                  80

Asp Ile Ala Thr Tyr Tyr Cys Gln His Phe Asp His Val Pro Arg Tyr
                85                  90                  95

Thr Phe Gly Pro Gly Thr Lys Val Asp Leu Lys
            100                 105

<210> SEQ ID NO 15
<211> LENGTH: 128
<212> TYPE: PRT
<213> ORGANISM: Homo sapiens
<220> FEATURE:
<221> NAME/KEY: PEPTIDE
<222> LOCATION: (1)..(128)
<223> OTHER INFORMATION: Clone 6a:5 VH

<400> SEQUENCE: 15

Ala Glu Val Gln Leu Leu Glu Ser Gly Pro Gly Leu Val Lys Pro Ser
1               5                   10                  15

Gln Thr Leu Ser Leu Thr Cys Ala Ile Ser Gly Asp Asn Val Ser Arg
            20                  25                  30

Lys Ser Ala Ala Trp Asn Trp Ile Arg Gln Ser Pro Ser Arg Gly Leu
        35                  40                  45

Glu Trp Leu Gly Arg Thr Tyr His Met Ser Lys Trp Tyr Ser Val Tyr
    50                  55                  60

Ala Thr Ser Leu Lys Ser Arg Ile Asn Ile Asn Val Asp Thr Ser Arg
65                  70                  75                  80

Asn Gln Phe Ala Leu Gln Leu Arg Ser Val Thr Pro Glu Asp Thr Ala
                85                  90                  95

Val Tyr Tyr Cys Ala Arg Glu Gly Pro Glu Trp Ala Val Gly Gly Thr
            100                 105                 110

Tyr Gly Met Asp Val Trp Gly Gln Gly Thr Thr Val Thr Val Ser Ser
        115                 120                 125

<210> SEQ ID NO 16
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 6a:5 VK

<400> SEQUENCE: 16

Ala Glu Leu Thr Gln Ser Pro Asp Thr Leu Ser Leu Ser Pro Gly Glu
1               5                   10                  15

Arg Ala Thr Leu Ser Cys Arg Ala Ser Gln Ser Val Asn Asn Asn Tyr
            20                  25                  30

```
Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Glu Thr Asp Phe Thr Leu Thr Ile Ser Arg Leu Glu Pro
 65                  70                  75                  80

Glu Asp Phe Ala Val Tyr Tyr Cys Gln Gln Tyr Asp Ser Ser Arg Thr
                 85                  90                  95

Phe Gly Gln Gly Thr Lys Val Glu Ile Lys
            100                 105
```

<210> SEQ ID NO 17
<211> LENGTH: 130
<212> TYPE: PRT
<213> ORGANISM: Homo sapiens
<220> FEATURE:
<221> NAME/KEY: PEPTIDE
<222> LOCATION: (1)..(130)
<223> OTHER INFORMATION: Clone 2a:2 VH

<400> SEQUENCE: 17

```
Ala Glu Val Gln Leu Leu Glu Gln Ser Gly Ala Glu Val Lys Lys Pro
 1               5                  10                  15

Gly Ala Ser Val Lys Val Ser Cys Lys Ala Ser Gly Tyr Thr Phe Thr
            20                  25                  30

Gly Tyr Tyr Met His Trp Val Arg Gln Ala Pro Gly Gln Gly Leu Glu
            35                  40                  45

Trp Met Gly Trp Ile Asn Pro Glu Ser Gly Ala Thr Asn Tyr Ala Gln
 50                  55                  60

Asn Phe Gln Gly Arg Val Thr Met Thr Thr Asp Thr Ser Met Arg Thr
 65                  70                  75                  80

Ala Tyr Ile Glu Val Ser Arg Leu Arg Ser Asp Asp Thr Ala Val Tyr
                 85                  90                  95

Phe Cys Ala Arg Gly Gly Ala Phe Cys Thr Gly Gly Thr Cys Tyr Phe
            100                 105                 110

Ala Ile Tyr Gly Met Asp Val Trp Gly Gln Gly Thr Ala Val Ile Val
            115                 120                 125

Ser Ser
 130
```

<210> SEQ ID NO 18
<211> LENGTH: 110
<212> TYPE: PRT
<213> ORGANISM: Homo sapiens
<220> FEATURE:
<221> NAME/KEY: PEPTIDE
<222> LOCATION: (1)..(110)
<223> OTHER INFORMATION: Clone 2a:2 VK

<400> SEQUENCE: 18

```
Ala Glu Leu Thr Gln Ser Pro Leu Ser Leu Pro Val Thr Pro Gly Glu
 1               5                  10                  15

Pro Ala Ser Ile Ser Cys Arg Ser Ser Gln Ser Leu Leu His Thr Asn
            20                  25                  30

Gly Tyr Asn Tyr Leu Asp Trp Tyr Leu Gln Lys Pro Gly Gln Ser Pro
            35                  40                  45

Gln Leu Leu Ile Tyr Leu Gly Ser Asn Arg Ala Ser Gly Val Pro Asp
 50                  55                  60
```

```
Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Met Gln Ala Leu
                 85                  90                  95

Gln Thr Leu Thr Phe Gly Gly Gly Thr Lys Val Glu Ile Lys
            100                 105                 110

<210> SEQ ID NO 19
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Clone 2a:4 VH

<400> SEQUENCE: 19

Ala Glu Val Gln Leu Leu Glu Ser Gly Gly Gly Leu Val Lys Pro Gly
 1               5                  10                  15

Gly Ser Leu Arg Leu Ser Cys Ala Ala Ser Gly Phe Thr Phe Ser Asn
                 20                  25                  30

Ala Trp Met Ser Trp Val Arg Gln Ala Pro Gly Lys Gly Leu Glu Trp
             35                  40                  45

Val Gly Arg Ile Lys Ser Lys Thr Asp Gly Gly Thr Ile Asp Tyr Ala
 50                  55                  60

Ala Pro Val Lys Gly Arg Phe Thr Ile Ser Arg Asp Asp Ser Lys Asn
 65                  70                  75                  80

Thr Leu Tyr Leu Gln Met Asn Ser Leu Lys Thr Glu Asp Thr Ala Val
             85                  90                  95

Tyr Tyr Cys Thr Thr Trp Asp Gly Asp His Ala Val Asp Tyr Trp Gly
            100                 105                 110

Gln Gly Thr Leu Val Thr Val Ser Ser
        115                 120

<210> SEQ ID NO 20
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:4 VK

<400> SEQUENCE: 20

Ala Glu Leu Thr Gln Ser Pro Ser Ser Leu Ser Ala Ser Ile Gly Asp
 1               5                  10                  15

Arg Val Ala Ile Ser Cys Gln Ala Ser Gln Asp Ile Gly Asn Tyr Leu
                 20                  25                  30

Asn Trp Tyr Gln Gln Lys Pro Gly Lys Ala Pro Arg Leu Leu Ile Tyr
             35                  40                  45

Asp Ala Ser Asn Leu Glu Ala Gly Val Pro Ser Arg Phe Ser Gly Ser
 50                  55                  60

Gly Ser Gly Thr Asp Phe Thr Leu Thr Ile Ser Thr Leu Gln Pro Glu
 65                  70                  75                  80

Asp Phe Ala Thr Phe Tyr Cys Gln Gln Thr Asp Ser Thr Pro Tyr Thr
             85                  90                  95

Phe Gly Gln Gly Thr Lys Leu Glu Ile Arg
            100                 105
```

```
<210> SEQ ID NO 21
<211> LENGTH: 120
<212> TYPE: PRT
<213> ORGANISM: Homo sapiens
<220> FEATURE:
<221> NAME/KEY: PEPTIDE
<222> LOCATION: (1)..(120)
<223> OTHER INFORMATION: Clone 2a:5 VH

<400> SEQUENCE: 21

Ala Glu Val Gln Leu Leu Glu Ser Gly Pro Gly Leu Val Lys Pro Ser
1               5                   10                  15

Glu Thr Leu Ser Leu Thr Cys Thr Val Ser Thr Gly Ser Ile Ser Gly
            20                  25                  30

Tyr Phe Trp Ser Trp Ile Arg Gln Pro Pro Gly Lys Gly Leu Glu Trp
        35                  40                  45

Ile Ala Tyr Ile His Asn Ser Gly Asn Thr Asn Tyr Asn Pro Ser Leu
    50                  55                  60

Arg Ser Arg Val Thr Val Ser Ile Asp Thr Ser Lys Asn Gln Phe Ser
65                  70                  75                  80

Leu Lys Leu Thr Ser Val Thr Ala Ala Asp Thr Ala Val Tyr Tyr Cys
                85                  90                  95

Ala Arg Asp Gly Gly Gly Trp Asp Thr Tyr Leu Asp Ser Trp Gly Gln
            100                 105                 110

Gly Phe Leu Val Thr Val Ser Ser
        115                 120

<210> SEQ ID NO 22
<211> LENGTH: 105
<212> TYPE: PRT
<213> ORGANISM: Homo sapiens
<220> FEATURE:
<221> NAME/KEY: PEPTIDE
<222> LOCATION: (1)..(105)
<223> OTHER INFORMATION: Clone 2a:5 VK

<400> SEQUENCE: 22

Ala Glu Leu Thr Gln Ser Pro Ser Ser Leu Ser Ala Ser Val Gly Asp
1               5                   10                  15

Arg Val Thr Ile Thr Cys Arg Ala Ser Gln Thr Val Ser Ser Tyr Leu
            20                  25                  30

Asn Trp Tyr Gln Gln Lys Pro Gly Lys Ala Pro Lys Val Leu Ile Tyr
        35                  40                  45

Gly Ile Ser Thr Leu Gln Ser Gly Val Pro Ser Arg Phe Ser Gly Ser
    50                  55                  60

Gly Ser Glu Thr Asp Phe Thr Leu Thr Ile Ser Asn Leu Gln Pro Glu
65                  70                  75                  80

Asp Phe Ala Ile Tyr Tyr Cys Gln Gln Ser Tyr Ser Ser Arg Thr Phe
                85                  90                  95

Gly Gln Gly Thr Lys Val Glu Ile Lys
            100                 105

<210> SEQ ID NO 23
<211> LENGTH: 120
<212> TYPE: PRT
<213> ORGANISM: Homo sapiens
<220> FEATURE:
<221> NAME/KEY: PEPTIDE
<222> LOCATION: (1)..(120)
<223> OTHER INFORMATION: Clone 2a:13 VH

<400> SEQUENCE: 23
```

Ala Glu Val Gln Leu Leu Glu Ser Gly Pro Gly Leu Val Lys Pro Ser
1               5                   10                  15

Glu Thr Leu Ser Leu Thr Cys Thr Val Ser Gly Gly Ser Ile Ser Asp
                20                  25                  30

Tyr Tyr Trp Ser Trp Ile Arg Gln Pro Pro Gly Lys Gly Leu Glu Trp
            35                  40                  45

Ile Gly His Thr Tyr Asp Asn Gly Gly Thr Lys Tyr Asn Pro Ser Leu
        50                  55                  60

Lys Ser Arg Ala Ser Ile Ser Val Asp Thr Ser Lys Asn Gln Val Ser
65                  70                  75                  80

Leu Arg Leu Thr Ser Val Thr Ala Ala Asp Thr Ala Val Tyr Tyr Cys
                85                  90                  95

Ala Thr Ala Phe Leu Asp Asn Ser Gly Trp Tyr Thr Phe Asp Ser Trp
            100                 105                 110

Gly Gln Gly Ser Leu Val Thr Val
            115                 120

<210> SEQ ID NO 24
<211> LENGTH: 109
<212> TYPE: PRT
<213> ORGANISM: Homo sapiens
<220> FEATURE:
<221> NAME/KEY: PEPTIDE
<222> LOCATION: (1)..(109)
<223> OTHER INFORMATION: Clone 2a:13 VK

<400> SEQUENCE: 24

Ala Glu Leu Thr Gln Ser Pro Ser Ser Val Ser Ala Ser Val Arg Asp
1               5                   10                  15

Arg Val Thr Ile Thr Cys Arg Ala Ser Gln Gly Ile Ser Thr Trp Leu
                20                  25                  30

Ala Trp Tyr Gln Gln Lys Pro Gly Lys Ala Pro Lys Leu Leu Ile Tyr
            35                  40                  45

Ala Ala Ser Thr Leu Gln Ser Gly Val Pro Ser Arg Phe Ser Gly Ser
        50                  55                  60

Gly Ser Gly Thr Asp Phe Thr Leu Thr Ile Gly Ser Leu Gln Pro Glu
65                  70                  75                  80

Asp Val Ala Thr Tyr Tyr Cys Gln Gln Ala Asn Ser Phe Pro Pro Gly
                85                  90                  95

Ala Leu Thr Phe Gly Gly Gly Thr Lys Val Glu Val Lys
            100                 105

<210> SEQ ID NO 25
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Clone 2a:14 VH

<400> SEQUENCE: 25

Ala Glu Val Gln Leu Leu Glu Gln Ser Gly Gly Val Val Gln Pro
1               5                   10                  15

Gly Arg Ser Leu Arg Leu Ser Cys Ala Ala Ser Gly Phe Thr Phe Ser
                20                  25                  30

Thr Tyr Ala Met His Trp Val Arg Gln Ala Pro Gly Lys Gly Leu Glu
            35                  40                  45

```
Trp Val Ala Val Ile Ser His Asp Gly Ser Asn Lys Phe Tyr Ala Asp
 50                  55                  60
Ser Val Lys Gly Arg Phe Thr Ile Ser Arg Asp Ser Ser Lys Asn Thr
 65                  70                  75                  80
Leu Tyr Leu Gln Met Asn Ser Leu Arg Pro Gly Asp Thr Ala Val Tyr
                 85                  90                  95
Tyr Cys Ser Arg Trp Asp Arg Arg Ala Glu Tyr Phe Gln Asp Trp Gly
            100                 105                 110
Gln Gly Thr Leu Val Thr Val Ser Ser
        115                 120
```

<210> SEQ ID NO 26
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:14 VK

<400> SEQUENCE: 26

```
Ala Glu Leu Thr Gln Ser Pro Ala Phe Met Ser Ala Thr Pro Gly Asp
 1               5                  10                  15
Lys Val Asn Ile Ser Cys Lys Ala Ser Gln Asp Ile Asp Asp Asp Met
             20                  25                  30
Asn Trp Tyr Gln Gln Lys Pro Gly Glu Ala Ala Ile Phe Ile Ile Gln
         35                  40                  45
Glu Ala Thr Thr Leu Val Pro Gly Ile Pro Pro Arg Phe Ser Gly Ser
 50                  55                  60
Gly Tyr Gly Thr Asp Phe Thr Leu Thr Ile Asn Asn Ile Glu Ser Glu
 65                  70                  75                  80
Asp Ala Ala Tyr Tyr Phe Cys Leu Gln His Asp Asn Phe Pro Leu Thr
                 85                  90                  95
Phe Gly Gln Gly Thr Lys Val Glu Ile Lys
            100                 105
```

<210> SEQ ID NO 27
<211> LENGTH: 118
<212> TYPE: PRT
<213> ORGANISM: Homo sapiens
<220> FEATURE:
<221> NAME/KEY: PEPTIDE
<222> LOCATION: (1)..(118)
<223> OTHER INFORMATION: Clone 2a:23 VH

<400> SEQUENCE: 27

```
Ala Glu Val Gln Leu Leu Glu Ser Gly Ala Gly Val Val Gln Pro Gly
 1               5                  10                  15
Lys Ser Leu Thr Leu Ser Cys Val Gly Ser Gly Phe Thr Phe Ser Ile
             20                  25                  30
Tyr Ala Met His Trp Val Arg Gln Ala Pro Gly Lys Gly Leu Glu Trp
         35                  40                  45
Val Ala Val Leu Ser Ser Asp Gly Ser Asn Asp Tyr Tyr Ala Asp Ser
 50                  55                  60
Val Lys Gly Arg Phe Ser Ile Phe Arg Asp Thr Ser Lys Asn Ser Leu
 65                  70                  75                  80
Asn Leu Leu Met Asn Asn Val Arg Gly Glu Asp Thr Ala Val Tyr Tyr
                 85                  90                  95
Cys Ala Arg Asp Gly Asp Gly Ser Phe Phe Tyr Trp Gly Gln Gly Thr
```

```
                100                 105                 110
Leu Val Thr Val Ser Ser
        115

<210> SEQ ID NO 28
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:23 VK

<400> SEQUENCE: 28

Ala Glu Leu Thr Gln Ser Pro Ala Phe Met Ser Ala Thr Pro Gly Asp
1               5                   10                  15

Lys Val Asn Ile Ser Cys Lys Ala Ser Gln Asp Ile Asp Asp Asp Met
            20                  25                  30

Asn Trp Tyr Gln Gln Lys Pro Gly Glu Ala Ala Ile Phe Ile Ile Gln
        35                  40                  45

Glu Ala Thr Thr Leu Val Pro Gly Ile Pro Pro Arg Phe Ser Gly Ser
50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Leu Gln His Asp Asn Phe Pro Leu Thr
                85                  90                  95

Phe Gly Gln Gly Thr Lys Val Glu Ile Lys
            100                 105

<210> SEQ ID NO 29
<211> LENGTH: 118
<212> TYPE: PRT
<213> ORGANISM: Homo sapiens
<220> FEATURE:
<221> NAME/KEY: PEPTIDE
<222> LOCATION: (1)..(118)
<223> OTHER INFORMATION: Clone 2a:25 VH

<400> SEQUENCE: 29

Ala Glu Val Gln Leu Leu Glu Gln Ser Gly Ala Glu Val Lys Lys Pro
1               5                   10                  15

Gly Ala Ser Val Lys Val Ser Cys Lys Ala Ser Gly Tyr Met Phe Thr
            20                  25                  30

Cys Tyr Tyr Met His Trp Val Arg Gln Ala Pro Gly Gln Gly Leu Glu
        35                  40                  45

Trp Met Gly Met Val Asn Pro Thr Gly Gly Ser Ser Tyr Ala Gln
50                  55                  60

Lys Phe Gln Gly Arg Val Thr Met Thr Lys Gly His Val Thr Ser Thr
65                  70                  75                  80

Val Tyr Met Glu Leu Ser Ser Leu Arg Ser Glu Asp Thr Ala Val Tyr
                85                  90                  95

Tyr Cys Ala Thr Gly Met Val Arg Gly Asp Glu Trp Gly Gln Gly Thr
            100                 105                 110

Leu Val Thr Val Ser Ser
        115

<210> SEQ ID NO 30
<211> LENGTH: 106
<212> TYPE: PRT
<213> ORGANISM: Homo sapiens
```

```
<220> FEATURE:
<221> NAME/KEY: PEPTIDE
<222> LOCATION: (1)..(106)
<223> OTHER INFORMATION: Clone 2a:25 VK

<400> SEQUENCE: 30

Ala Glu Leu Thr Gln Ser Pro Ser Phe Ser Ser Ala Ser Val Gly Asp
 1               5                  10                  15

Arg Val Thr Ile Thr Cys Arg Ala Ser His Gly Ile Ser His Leu
                20                  25                  30

Ala Trp Phe Gln His Lys Pro Gly Lys Ala Pro Asn Leu Leu Ile Tyr
                35                  40                  45

Ala Ala Ser Thr Leu Gln Ser Gly Val Pro Ser Arg Phe Ser Gly Ser
            50                  55                  60

Gln Ser Gly Thr Glu Phe Thr Leu Thr Ile Thr Ser Leu His Pro Glu
65                  70                  75                  80

Asp Phe Ala Thr Tyr Tyr Cys Gln Gln Leu Tyr Thr Trp Pro Met Gly
                85                  90                  95

Phe Gly Gln Gly Thr Arg Leu Glu Ile Thr
            100                 105

<210> SEQ ID NO 31
<211> LENGTH: 126
<212> TYPE: PRT
<213> ORGANISM: Homo sapiens
<220> FEATURE:
<221> NAME/KEY: PEPTIDE
<222> LOCATION: (1)..(126)
<223> OTHER INFORMATION: Clone 2a:30 VH

<400> SEQUENCE: 31

Ala Glu Val Gln Leu Leu Glu Gln Ser Gly Gly Gly Leu Val Gln Pro
 1               5                  10                  15

Gly Gly Ser Leu Arg Leu Ser Cys Thr Ala Ser Gly Phe Thr Leu Thr
                20                  25                  30

Asp Tyr Ser Met Asp Trp Val Arg Gln Ala Pro Gly Lys Gly Pro Glu
            35                  40                  45

Trp Val Gly Arg Ser Arg Asn Lys Ala Asn Ile Tyr Thr Thr Glu Tyr
        50                  55                  60

Ala Ala Ser Val Lys Gly Arg Phe Val Ile Ser Arg Asp Asp Ser Glu
65                  70                  75                  80

Asn Ser Val Tyr Leu Gln Met Asn Asn Val Lys Met Asp Asp Thr Ala
                85                  90                  95

Val Tyr Tyr Cys Ala Arg Gly Glu Gly Ile Phe Tyr Gly Ser Gly Ser
            100                 105                 110

Leu Asp Leu Trp Gly Gln Gly Ala Val Val Thr Val Ser Ser
        115                 120                 125

<210> SEQ ID NO 32
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:30 VK

<400> SEQUENCE: 32

Ala Glu Leu Thr Gln Ser Pro Ser Ser Leu Ser Ala Ser Val Gly Asp
 1               5                  10                  15
```

```
Arg Val Thr Ile Thr Cys Arg Ser Gln Ser Ile Ser Asn Ser Leu
            20                  25                  30

His Trp Phe Gln Gln Glu Pro Gly Lys Ala Pro Lys Leu Leu Ile Tyr
            35                  40                  45

Ala Ala Ser Thr Leu Gln Ser Gly Val Pro Ser Arg Phe Ser Gly Ser
            50                  55                  60

Gly Ser Gly Thr Asp Phe Thr Leu Ile Ile Thr Gly Leu Gln Pro Glu
 65                  70                  75                  80

Asp Phe Ala Thr Tyr Tyr Cys Gln Gln Ser Pro Arg Thr Pro Leu Thr
                85                  90                  95

Phe Gly Gly Gly Thr Lys Val Glu Ile Arg
            100                 105

<210> SEQ ID NO 33
<211> LENGTH: 126
<212> TYPE: PRT
<213> ORGANISM: Homo sapiens
<220> FEATURE:
<221> NAME/KEY: PEPTIDE
<222> LOCATION: (1)..(126)
<223> OTHER INFORMATION: Clone 2a:32 VH

<400> SEQUENCE: 33

Ala Glu Val Gln Leu Leu Glu Gln Ser Gly Gly Asp Leu Val Lys Pro
 1               5                  10                  15

Gly Gly Ser Leu Arg Leu Ser Cys Ala Ala Ser Gly Phe Thr Phe Thr
            20                  25                  30

Asp Tyr Tyr Met Asn Trp Ile Arg Gln Ala Pro Gly Lys Gly Leu Glu
            35                  40                  45

Trp Ile Ala Tyr Ile Ser Ile Gly Ser Asp Asp Thr Lys Tyr Ala Ala
            50                  55                  60

Ser Val Lys Gly Arg Phe Ser Ile Ser Arg Asp Asn Ala Lys Asn Ser
 65                  70                  75                  80

Leu Tyr Leu Gln Met Asn Ser Leu Arg Val Glu Asp Thr Ala Val Tyr
                85                  90                  95

Tyr Cys Gly Arg Gly Gly Gly Tyr Cys Ser Gly Gly Asn Cys Tyr Ser
            100                 105                 110

Ser Asp Tyr Trp Gly Gln Gly Ala Leu Val Thr Val Ser Ser
            115                 120                 125

<210> SEQ ID NO 34
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:32 VK

<400> SEQUENCE: 34

Ala Glu Leu Thr Gln Ser Pro Ser Ser Leu Ser Ala Phe Thr Gly Asp
 1               5                  10                  15

Arg Val Ser Ile Thr Cys Arg Ala Ser Gln Gly Ile Gly Asn Ser Leu
            20                  25                  30

Ala Trp Tyr Gln Gln Lys Pro Gly His Val Pro Lys Val Leu Ile Tyr
            35                  40                  45

Asp Ala Ser Thr Leu Ser Ser Gly Ala Pro Ser Arg Phe Ser Gly Ser
            50                  55                  60

Gly Ser Gly Thr Asp Phe Thr Leu Thr Ile Ser Gly Leu Gln Pro Glu
```

```
                65                  70                  75                  80
Asp Val Ala Thr Tyr Tyr Cys Gln Lys Tyr Lys Ser Ala Pro Leu Thr
                    85                  90                  95

Phe Gly Gly Gly Thr Lys Val Glu Ile Arg
                100                 105
```

<210> SEQ ID NO 35
<211> LENGTH: 131
<212> TYPE: PRT
<213> ORGANISM: Homo sapiens
<220> FEATURE:
<221> NAME/KEY: PEPTIDE
<222> LOCATION: (1)..(131)
<223> OTHER INFORMATION: Clone 2a:33 VH

<400> SEQUENCE: 35

```
Ala Glu Val Gln Leu Leu Glu Gln Ser Gly Gly Gly Leu Val Gln Pro
1               5                   10                  15

Gly Arg Ser Leu Arg Leu Ser Cys Ala Ala Ser Gly Phe Thr Phe Asp
                20                  25                  30

Asp Tyr Ala Met His Trp Val Arg Gln Thr Pro Gly Lys Gly Leu Glu
            35                  40                  45

Trp Val Ser Gly Ile Gly Trp Asn Ser Gly Thr Ile Glu Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Pro Glu Asp Thr Ala Leu Tyr
                85                  90                  95

Tyr Cys Ala Lys Asp Leu His Ser Phe Gly Tyr Cys Ser Gly Arg Ser
                100                 105                 110

Cys Tyr Phe His Pro Phe Asp Tyr Trp Gly Gln Gly Thr Leu Val Thr
            115                 120                 125

Val Ser Ser
        130
```

<210> SEQ ID NO 36
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: Clone 2a:33 VK

<400> SEQUENCE: 36

```
Ala Glu Leu Thr Gln Ser Pro Asp Ser Leu Ala Val Ser Leu Gly Glu
1               5                   10                  15

Arg Ala Thr Ile Asn Cys Lys Ser Ser Gln Ser Val Leu Ser Ser Ser
                20                  25                  30

Asn Asn Lys Asn Tyr Leu Ala Trp Tyr Gln Gln Lys Pro Arg Gln Pro
            35                  40                  45

Pro Lys Leu Leu Ile Tyr Trp Ala Ser Thr Arg Glu Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Phe
                85                  90                  95

Tyr Ser Thr Pro Pro Thr Phe Gly Gly Gly Thr Lys Val Glu Ile Arg
                100                 105                 110
```

```
<210> SEQ ID NO 37
<211> LENGTH: 118
<212> TYPE: PRT
<213> ORGANISM: Homo sapiens
<220> FEATURE:
<221> NAME/KEY: PEPTIDE
<222> LOCATION: (1)..(118)
<223> OTHER INFORMATION: Clone 2a:37 VH

<400> SEQUENCE: 37

Ala Glu Val Gln Leu Leu Glu Ser Gly Gly Gly Leu Val Gln Pro Gly
1               5                   10                  15

Arg Ser Leu Arg Leu Ser Cys Ala Ala Ser Gly Phe Thr Phe Ser Asn
            20                  25                  30

Ser Asp Met His Trp Val Arg Gln Ala Pro Gly Lys Gly Leu Glu Trp
        35                  40                  45

Val Thr Val Ser Ser Arg Asp Gly Tyr Asp Asn Tyr Tyr Ala Asp Ser
65                  70                  75                  80

Val Arg Gly Arg Phe Thr Ile Ser Arg Asp Asn Ser Lys Asn Thr Leu
65                  70                  75                  80

Tyr Leu Gln Met Asn Thr Leu Arg Ala Glu Asp Thr Ala Val Tyr Tyr
            85                  90                  95

Cys Ala Lys Arg Arg Gly Tyr Ala Phe Asp Ile Trp Gly Gln Gly Thr
        100                 105                 110

Met Val Thr Val Ser Ser
        115

<210> SEQ ID NO 38
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:37 VK

<400> SEQUENCE: 38

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Asn Thr Tyr Leu
            20                  25                  30

Asn Trp Tyr Gln Gln Lys Pro Gly Lys Ala Pro Glu Leu Leu Ile Tyr
        35                  40                  45

Gly Ala Ser Ser Leu Gln Ser Gly Val Pro Ser Arg Phe Ser Gly Ser
    50                  55                  60

Gly Ser Gly Thr Asp Phe Thr Leu Thr Ile Thr Ser Leu Gln Ala Glu
65                  70                  75                  80

Asp Phe Ala Ser Tyr Phe Cys Gln Gln Ser Asp Ser Thr Pro Arg Thr
            85                  90                  95

Phe Gly Gln Gly Thr Lys Val Glu Ile Lys
        100                 105

<210> SEQ ID NO 39
<211> LENGTH: 128
<212> TYPE: PRT
<213> ORGANISM: Homo sapiens
<220> FEATURE:
<221> NAME/KEY: PEPTIDE
<222> LOCATION: (1)..(128)
<223> OTHER INFORMATION: Clone 2a:40 VH
```

<400> SEQUENCE: 39

```
Ala Glu Val Gln Leu Leu Glu Gln Ser Gly Gly Gly Leu Val Lys Pro
1               5                   10                  15

Gly Gly Ser Leu Arg Leu Ser Cys Thr Ala Ser Gly Phe Thr Phe Ser
            20                  25                  30

Gly Phe Thr Phe Ser Asp His Tyr Met Ser Trp Ile Arg Gln Ala Pro
        35                  40                  45

Gly Lys Gly Leu Glu Leu Val Ser Tyr Ile Ile Ser Asn Gly Tyr Thr
    50                  55                  60

Asn Tyr Pro Asp Ser Val Lys Gly Arg Phe Thr Val Ser Arg Asp Asn
65                  70                  75                  80

Ala Arg Lys Ser Leu Tyr Leu Gln Met Asn Ser Leu Arg Val Glu Asp
                85                  90                  95

Thr Ala Ile Tyr Tyr Cys Ala Arg Gly Leu Ser Pro Ser Ile Ala Gly
                100                 105                 110

Asp Gly Phe Asp Ile Trp Gly Gln Gly Thr Met Val Thr Val Ser Ser
            115                 120                 125
```

<210> SEQ ID NO 40
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2a:40 VK

<400> SEQUENCE: 40

```
Ala Glu Leu Thr Gln Ser Pro Ala Phe Met Ser Ala Thr Pro Gly Asp
1               5                   10                  15

Lys Val Asn Ile Ser Cys Lys Ala Ser Gln Asp Ile Asp Asp Asp Met
            20                  25                  30

Asn Trp Tyr Gln Gln Lys Pro Gly Glu Ala Ala Ile Phe Ile Ile Gln
        35                  40                  45

Glu Ala Thr Thr Leu Val Pro Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Leu Gln His Asp Asn Phe Pro Leu Thr
                85                  90                  95

Phe Gly Gln Gly Thr Lys Val Glu Ile Lys
                100                 105
```

<210> SEQ ID NO 41
<211> LENGTH: 116
<212> TYPE: PRT
<213> ORGANISM: Homo sapiens
<220> FEATURE:
<221> NAME/KEY: PEPTIDE
<222> LOCATION: (1)..(116)
<223> OTHER INFORMATION: Clone 2b:1 VH

<400> SEQUENCE: 41

```
Ala Glu Val Gln Leu Leu Glu Ser Gly Pro Arg Leu Val Lys Pro Ser
1               5                   10                  15

Gln Thr Leu Ser Leu Thr Cys Thr Val Ser Gly Asp Ser Leu Asn Asn
            20                  25                  30

Ala Ser His Tyr Trp Ala Trp Ile Arg Gln Pro Ala Gly Lys Gly Leu
```

-continued

```
                35                  40                  45
Glu Trp Ile Gly Arg Ile His Arg Gly Gly Ser Thr Asn Tyr Asn Pro
             50                  55                  60
Ser Leu Gln Ser Arg Val Thr Ile Ser Met Asp Glu Ser Lys Asn Gln
 65                  70                  75                  80
Phe Ser Leu Arg Leu Asn Ser Val Thr Ala Ala Asp Thr Ala Val Tyr
                 85                  90                  95
Tyr Cys Ala Arg Asp Pro Pro Lys Ala Trp Gly Pro Gly Ile Leu Val
            100                 105                 110
Thr Val Ser Ser
        115

<210> SEQ ID NO 42
<211> LENGTH: 105
<212> TYPE: PRT
<213> ORGANISM: Homo sapiens
<220> FEATURE:
<221> NAME/KEY: PEPTIDE
<222> LOCATION: (1)..(105)
<223> OTHER INFORMATION: Clone 2b:1 VK

<400> SEQUENCE: 42

Ala Glu Leu Thr Gln Ser Pro Ser Ser Leu Ser Ala Ser Val Gly Asp
 1               5                  10                  15
Arg Val Thr Ile Ala Cys Arg Ala Ser Gln Ser Ile Ser Asn His Leu
                20                  25                  30
Asn Trp Tyr Gln Gln Lys Pro Gly Lys Ala Pro Lys Val Leu Ile Tyr
             35                  40                  45
Ala Ala Ser Ser Leu Gln Ser Gly Val Pro Ser Arg Phe Ser Gly Ser
         50                  55                  60
Gly Ser Gly Thr Asp Phe Thr Leu Thr Ile Ser Ser Leu Gln Pro Glu
 65                  70                  75                  80
Asp Phe Ala Ile Tyr Tyr Cys Gln Gln Ser Tyr Ser Asn Ala Asp Phe
                 85                  90                  95
Gly Pro Gly Thr Lys Val Asp Ile Lys
            100                 105

<210> SEQ ID NO 43
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Clone 2b:3 VH

<400> SEQUENCE: 43

Ala Glu Val Gln Leu Leu Glu Ser Gly Ala Glu Val Lys Lys Pro Gly
 1               5                  10                  15
Ala Ser Val Thr Val Ser Cys Lys Ala Ser Gly Tyr Ser Phe Ser Asp
                20                  25                  30
Tyr Tyr Ile His Trp Val Arg Gln Ala Pro Gly Gln Gly Leu Glu Trp
             35                  40                  45
Met Gly Ile Ile Asn Pro Ser Ala Gly Thr Thr Thr Tyr Lys Gln Lys
         50                  55                  60
Phe Gln His Arg Val Thr Leu Thr Arg Asp Thr Ser Thr Asn Thr Ala
 65                  70                  75                  80
Tyr Met Lys Leu Tyr Asn Leu Thr Pro Asp Asp Thr Ala Ile Phe Phe
                 85                  90                  95
```

-continued

Cys Ala Arg Gly Ser Gly Gly Ser Arg Ser Glu Tyr Asp Tyr Trp Gly
                100                 105                 110

Gln Gly Thr Leu Val Thr Val Ser Ser
        115                 120

<210> SEQ ID NO 44
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2b:3 VK

<400> SEQUENCE: 44

Ala Glu Leu Thr Gln Ser Pro Ser Ser Leu Ser Ala Ser Val Gly Asp
1               5                   10                  15

Gly Val Thr Ile Thr Cys Arg Ala Ser Gln Ser Ile Ser Thr Tyr Leu
            20                  25                  30

Asn Trp Tyr Gln Gln Lys Pro Gly Lys Ala Pro Lys Leu Leu Met Tyr
        35                  40                  45

Ala Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Ala Tyr Tyr Cys Gln Gln Ala Arg Ser Phe Pro Tyr Thr
                85                  90                  95

Phe Gly Gln Gly Thr Arg Leu Glu Ile Arg
            100                 105

<210> SEQ ID NO 45
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Clone 2b:4 VH

<400> SEQUENCE: 45

Ala Glu Val Gln Leu Leu Glu Ser Gly Gly Glu Val Lys Lys Pro Gly
1               5                   10                  15

Ser Ser Val Lys Val Ser Cys Lys Ala Ser Gly Gly Pro Phe Ser Ser
            20                  25                  30

Tyr Ala Ile His Trp Val Arg Gln Ala Pro Gly Gln Gly Leu Glu Trp
        35                  40                  45

Met Gly Ala Ile Ile Pro Phe Leu Gly Arg Ala Lys Tyr Ala Gln Lys
    50                  55                  60

Phe Glu Gly Arg Val Thr Ile Thr Ala Asp Gly Ser Met Ser Thr Ala
65                  70                  75                  80

Tyr Met Glu Val Ser Ser Leu Arg Ser Asp Asp Thr Ala Met Tyr Tyr
                85                  90                  95

Cys Ala Arg Asp Arg Gly Glu Leu Leu Leu Arg Met Asp Val Trp Gly
                100                 105                 110

Gln Gly Thr Ala Val Thr Val Ser Ser
        115                 120

<210> SEQ ID NO 46
<211> LENGTH: 106

```
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2b:4 VK

<400> SEQUENCE: 46
```

Ala Glu Leu Thr Gln Ser Pro Ala Phe Met Ser Ala Thr Pro Gly Asp
1               5                   10                  15

Lys Val Asn Ile Ser Cys Lys Ala Ser Gln Asp Ile Asp Asp Asp Met
            20                  25                  30

Asn Trp Tyr Gln Gln Lys Pro Gly Glu Ala Ala Ile Phe Ile Ile Gln
        35                  40                  45

Glu Ala Thr Thr Leu Val Pro Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Leu Gln His Asp Asn Phe Pro Leu Thr
                85                  90                  95

Phe Gly Gln Gly Thr Lys Val Glu Ile Lys
            100                 105

```
<210> SEQ ID NO 47
<211> LENGTH: 128
<212> TYPE: PRT
<213> ORGANISM: Homo sapiens
<220> FEATURE:
<221> NAME/KEY: PEPTIDE
<222> LOCATION: (1)..(128)
<223> OTHER INFORMATION: Clone 2b:5 VH

<400> SEQUENCE: 47
```

Ala Glu Val Gln Leu Leu Glu Ser Gly Gly Val Val Gln Pro Gly
1               5                   10                  15

Arg Ser Leu Arg Leu Ser Cys Ala Ala Ser Gly Phe Thr Leu Ser Thr
            20                  25                  30

Tyr Ala Met His Trp Val Arg Gln Ala Pro Gly Arg Gly Leu Glu Trp
        35                  40                  45

Val Ala Val Ile Ser Tyr Asp Gly Asp His Lys Phe Tyr Ala Asp Ser
    50                  55                  60

Met Lys Gly Arg Phe Ala Ile Ser Arg Asp Thr Ser Thr Asn Thr Leu
65                  70                  75                  80

Tyr Leu Glu Val Asn Ser Leu Lys Ile Glu Asp Thr Ala Val Tyr Tyr
                85                  90                  95

Cys Ala Arg Asp Arg Asp Arg Gly Gly Tyr Val Phe Ser Thr Thr
            100                 105                 110

Gly Gly Leu Asp Ser Trp Gly Gln Gly Thr Leu Val Thr Val Ser Ser
        115                 120                 125

```
<210> SEQ ID NO 48
<211> LENGTH: 111
<212> TYPE: PRT
<213> ORGANISM: Homo sapiens
<220> FEATURE:
<221> NAME/KEY: PEPTIDE
<222> LOCATION: (1)..(111)
<223> OTHER INFORMATION: Clone 2b:5 VK

<400> SEQUENCE: 48
```

Ala Glu Leu Thr Gln Ser Pro Leu Ser Leu Ala Val Thr Pro Gly Glu

```
                   1               5                  10                 15

Pro Ala Ser Ile Ser Cys Arg Thr Ser Gln Ser Leu Leu His Ser Asn
                    20                 25                 30

Gly Tyr Thr Tyr Leu Asp Trp Tyr Leu Gln Lys Pro Gly Gln Ser Pro
                    35                 40                 45

Gln Leu Leu Ile Tyr Leu Ala Ser Asn Arg Ala Ser Gly Val Pro Asp
    50                 55                 60

Arg Phe Ser Gly Ser Gly Ser Gly Thr Asp Phe Thr Leu Glu Ile Ser
65                  70                 75                 80

Arg Val Glu Ala Glu Asp Val Gly Val Tyr Tyr Cys Met Gln Pro Leu
                    85                 90                 95

Gln Thr Pro Val Thr Phe Gly Gln Gly Thr Lys Val Glu Val Lys
                    100                105                110

<210> SEQ ID NO 49
<211> LENGTH: 123
<212> TYPE: PRT
<213> ORGANISM: Homo sapiens
<220> FEATURE:
<221> NAME/KEY: PEPTIDE
<222> LOCATION: (1)..(123)
<223> OTHER INFORMATION: Clone 2b:7 VH

<400> SEQUENCE: 49

Ala Glu Val Gln Leu Leu Gln Ser Gly Ala Glu Val Lys Lys Pro
1               5                  10                 15

Gly Glu Ser Leu Lys Ile Ser Cys Arg Ala Ser Gly Tyr Ser Phe Ser
                    20                 25                 30

Leu Phe Trp Val Ala Trp Val Arg Gln Met Pro Gly Gln Gly Leu Glu
                    35                 40                 45

Trp Met Ala Ile Ile Tyr Pro Gly Asp Ser Asp Thr Thr Tyr Ser Pro
    50                 55                 60

Ser Phe Glu Gly Gln Val Asn Val Ser Val Asp Lys Pro Ile Ser Thr
65                  70                 75                 80

Ala Tyr Leu Gln Trp Ser Ser Leu Lys Ala Ser Asp Thr Ala Met Tyr
                    85                 90                 95

Tyr Cys Ala Arg Arg Ser Ser Asp Arg Arg Asp Ala Phe Asp Ile
                    100                105                110

Trp Gly Pro Gly Thr Met Val Thr Val Ser Ser
        115                120

<210> SEQ ID NO 50
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2b:7 VK

<400> SEQUENCE: 50

Ala Glu Leu Thr Gln Ser Pro Ala Phe Met Ser Ala Thr Pro Gly Asp
1               5                  10                 15

Lys Val Asn Ile Ser Cys Lys Ala Ser Gln Asp Ile Asp Asp Asp Met
                    20                 25                 30

Asn Trp Tyr Gln Gln Lys Pro Gly Glu Ala Ala Ile Phe Ile Ile Gln
                    35                 40                 45

Glu Ala Thr Thr Leu Val Pro Gly Ile Pro Pro Arg Phe Ser Gly Ser
    50                 55                 60
```

```
Gly Tyr Gly Thr Asp Phe Thr Leu Thr Ile Asn Asn Ile Glu Ser Glu
 65                  70                  75                  80

Asp Ala Ala Tyr Tyr Phe Cys Leu Gln His Asp Asn Phe Pro Leu Thr
                 85                  90                  95

Phe Gly Gln Gly Thr Lys Val Glu Ile Lys
            100                 105

<210> SEQ ID NO 51
<211> LENGTH: 128
<212> TYPE: PRT
<213> ORGANISM: Homo sapiens
<220> FEATURE:
<221> NAME/KEY: PEPTIDE
<222> LOCATION: (1)..(128)
<223> OTHER INFORMATION: Clone 2b:9 VH

<400> SEQUENCE: 51

Ala Glu Val Gln Leu Leu Glu Ser Gly Pro Gly Leu Val Gln Pro Ser
 1               5                  10                  15

Gln Thr Leu Ser Leu Thr Tyr Ala Ile Ser Gly Asp Ser Val Ser Ser
                 20                  25                  30

Asn Ser Ala Ala Trp Thr Trp Ile Arg Gln Ser Pro Ser Arg Gly Leu
             35                  40                  45

Glu Trp Leu Gly Met Thr Tyr Tyr Arg Ser Gln Trp Tyr His Glu Tyr
     50                  55                  60

Ala Val Ser Leu Lys Ser Arg Ile Thr Ile Asn Ala Asp Thr Ser Asn
 65                  70                  75                  80

Asn Gln Phe Ser Leu Gln Val Asn Ser Val Thr Pro Glu Asp Thr Ala
                 85                  90                  95

Leu Tyr Tyr Cys Ala Arg Ala Arg Phe Val Gly Asp Thr Thr Gly Tyr
                100                 105                 110

Tyr Thr Phe Asp Tyr Trp Gly Gln Gly Thr Leu Val Thr Val Ser Ser
            115                 120                 125

<210> SEQ ID NO 52
<211> LENGTH: 107
<212> TYPE: PRT
<213> ORGANISM: Homo sapiens
<220> FEATURE:
<221> NAME/KEY: PEPTIDE
<222> LOCATION: (1)..(107)
<223> OTHER INFORMATION: Clone 2b:9 VK

<400> SEQUENCE: 52

Ala Glu Leu Thr Gln Ser Pro Gly Thr Leu Ser Leu Ser Pro Gly Glu
 1               5                  10                  15

Arg Gly Thr Leu Ser Cys Arg Ala Ser Gln Ser Val Ser Ser Ser Tyr
                 20                  25                  30

Leu Ala Trp Tyr Gln Gln Lys Ala Gly Gln Ala Pro Arg Leu Leu Ile
             35                  40                  45

Tyr Gly Ala Ser Ser Arg Ala Thr Gly Ile Pro Asp Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Arg Tyr Gly Thr Ser Pro Lys
                 85                  90                  95

Thr Phe Gly Gln Gly Thr Lys Val Glu Phe Lys
            100                 105
```

```
<210> SEQ ID NO 53
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: Clone 2b:10 VH

<400> SEQUENCE: 53
```

Ala Glu Val Gln Leu Leu Glu Ser Gly Gly Val Val Gln Pro Gly
1               5                   10                  15

Arg Ser Leu Lys Leu Ser Cys Thr Ala Ser Thr Phe Thr Phe Thr Asn
            20                  25                  30

Tyr Ala Met His Trp Val Arg Gln Ala Pro Gly Lys Gly Leu Glu Trp
            35                  40                  45

Val Ala Leu Ile Ser Asn Asp Gly Ser Lys Thr Tyr Tyr Thr Asp Ser
50                  55                  60

Val Arg Gly Arg Phe Thr Ile Ser Arg Asp Asn Ser Lys Asn Thr Leu
65                  70                  75                  80

Phe Leu Gln Met Asn Ser Leu Arg Thr Glu Asp Thr Ala Val Tyr His
                85                  90                  95

Cys Ala Arg Val Lys Leu Gln Gly Ser Phe Asn Val Tyr Tyr Tyr Tyr
            100                 105                 110

Gly Leu Asp Val Trp Gly Gln Gly Thr Thr Val Thr Val Ser Ser
            115                 120                 125

```
<210> SEQ ID NO 54
<211> LENGTH: 110
<212> TYPE: PRT
<213> ORGANISM: Homo sapiens
<220> FEATURE:
<221> NAME/KEY: PEPTIDE
<222> LOCATION: (1)..(110)
<223> OTHER INFORMATION: Clone 2b:10 VK

<400> SEQUENCE: 54
```

Ala Glu Leu Thr Gln Ser Pro Leu Ser Leu Pro Val Thr Pro Gly Glu
1               5                   10                  15

Pro Ala Ser Ile Ser Cys Arg Ser Ser Gln Ser Leu Leu His Ser Asp
            20                  25                  30

Gly Tyr Asn Tyr Phe Asp Trp Tyr Leu Gln Lys Pro Gly Gln Ser Pro
            35                  40                  45

Gln Leu Leu Ile Tyr Leu Gly Ser Asn Arg Ala Ser Gly Val Pro Asp
50                  55                  60

Arg Phe Ser Gly Ser Gly Ser Asp Thr Asp Phe Thr Leu Lys Ile Ser
65                  70                  75                  80

Arg Val Glu Ala Glu Asp Val Gly Val Tyr Tyr Cys Met Gln Thr Leu
                85                  90                  95

Gln Thr Leu Thr Phe Gly Gly Gly Thr Lys Leu Glu Ile Lys
            100                 105                 110

```
<210> SEQ ID NO 55
<211> LENGTH: 118
<212> TYPE: PRT
<213> ORGANISM: Homo sapiens
<220> FEATURE:
<221> NAME/KEY: PEPTIDE
<222> LOCATION: (1)..(118)
<223> OTHER INFORMATION: Clone 2b:17 VH
```

```
<400> SEQUENCE: 55

Ala Glu Val Gln Leu Leu Glu Ser Gly Gly Gly Leu Val Gln Pro Gly
1               5                   10                  15

Arg Ser Leu Arg Leu Ser Cys Ala Ala Ser Gly Phe Thr Phe Ser Asn
                20                  25                  30

Ser Asp Met His Trp Val Arg Gln Ala Pro Gly Lys Gly Leu Glu Trp
            35                  40                  45

Val Thr Val Ser Ser Arg Asp Gly Tyr Asp Asn Tyr Tyr Ala Asp Ser
        50                  55                  60

Val Arg Gly Arg Phe Thr Ile Ser Arg Asp Asn Ser Lys Asn Thr Leu
65                  70                  75                  80

Tyr Leu Gln Met Asn Thr Leu Arg Ala Glu Asp Thr Ala Val Tyr Tyr
                85                  90                  95

Cys Ala Lys Arg Arg Gly Tyr Ala Phe Asp Ile Trp Gly Gln Gly Thr
                100                 105                 110

Met Val Thr Val Ser Ser
            115

<210> SEQ ID NO 56
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Clone 2b:17 VK

<400> SEQUENCE: 56

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Asn Thr Tyr Leu
                20                  25                  30

Asn Trp Tyr Gln Gln Lys Pro Gly Lys Ala Pro Glu Leu Leu Ile Tyr
            35                  40                  45

Gly Ala Ser Ser Leu Gln Ser Gly Val Pro Ser Arg Phe Ser Gly Ser
        50                  55                  60

Gly Ser Gly Thr Asp Phe Thr Leu Thr Ile Thr Ser Leu Gln Ala Glu
65                  70                  75                  80

Asp Phe Ala Ser Tyr Phe Cys Gln Gln Ser Asp Ser Thr Pro Arg Thr
                85                  90                  95

Phe Gly Gln Gly Thr Lys Val Glu Ile Lys
                100                 105
```

MATERIALS AND METHODS FOR TREATMENT OF HEPATITIS C

This application is a divisional application of U.S. patent application Ser. No. 10/466,242, filed Jan. 16, 2004, now U.S. Pat. No. 7,250,166, issued Jul. 31, 2007, which is a §371 Application of PCT/SE02/00044, filed Jan. 14, 2002, which in turn claims priority to U.S. Provisional Application No. 60/260,889, filed Jan. 12, 2001. Each of the foregoing applications is incorporated herein by reference as though set forth in full.

FIELD OF THE INVENTION

The present invention relates to materials and methods for treatment of hepatitis C. More closely, the invention relates to human monoclonal antibodies against HCV E1 antigen, to a reagent comprising such antibodies, and to vaccine compositions comprising such antibodies for passive immunisation. Furthermore, the invention relates to a method of treating or preventing HCV infection by administration of a vaccine composition comprising the monoclonal antibodies of the invention for passive immunisation.

BACKGROUND OF THE INVENTION

Human monoclonal antibodies have been assumed as attractive agents for antagonist effects in many medical applications: anti-toxins, anti-receptor molecules, anti-cytokine reagents to reduce or abolish an inflammatory response, etc.

Hepatitis C virus (HCV) is a major global health problem, with at least 170 million people infected the world over. HCV results in a chronic infection in 75-80% of those initially infected (Houghton 1996). Very likely, immunological factors influence whether the infection will resolve spontaneously or become chronic. The latter will result in a liver inflammation of variable degree, an inflammation that after 10-20 years may result in cirrhosis (20% of chronic cases), and hepatocellular cancer (HCC; approx. 20% of those with cirrhosis) (Houghton 1996). Current pharmaceutical treatment will fail in 60% of the cases (alpha-interferon+Ribavirin). Thus, there is a need for improved therapy.

HCV was discovered in 1989. Scientific studies have been severely hampered by the fact that there is no robust method to propagate the virus in vitro. Thus, substances cannot be tested for the capacity to block infection by the virus (neutralization assay). Similarly, the only animal model available is chimpanzee, also limiting the number of studies possible (by cost, availability of animals, etc.). As a substitute for a neutralisation assay, the inhibition of binding of one of the two envelope proteins (E2) to target cells has been developed. This is called the NOB assay: neutralisation of binding. Recently, a replicon system where a subgenomic portion of the viral genome replicates inside cells (but is not assembled into viral particles) has been developed, and optimized.

As mentioned previously, the immune system may have an important role in determining the course of the infection. Both the cellular immune response, as well as the humoral immune system, have been implicated as important for the outcome of the HCV infection. The relative importance of them is still disputed.

Whether the humoral immune response (i.e. specific B-lymphocytes and antibodies) can interfere with the clinical course of the disease have gained increasing attention over the last years:

1. The kinetics of antibodies to the hypervariable region (HVR) of E2 (one of the envelope glyco proteins) may be important: early occurrence of anti-HVR antibodies correlate with resolution of the acute infection.
2. Polyclonal anti-HCV immunoglobulin preparations given to liver transplanted patients decreased the occurrence of re-infection by HCV from 94% to 54%.
3. Polyclonal anti-HCV given to infected chimpanzees modulated (ameliorated) the course of the infection.
4. Individuals lacking immunoglobulin have a tendency to get a more severe and fast progressing disease compared to immunocompetent individuals.
5. Anti-HCV antibodies (particularly NOB positive antibodies) correlated with protection in vaccination experiments.

Accordingly, several groups and companies are currently exploring the possibilities of affecting the course of the infection by administration of anti-HCV antibodies, both to already infected and for prophylaxis (Burioni et al., 1998).

The present inventors have already cloned human antibodies to conserved regions of one of the two envelope proteins, E2 (Allander et al., 2000). These antibodies have NOB activity, and a patent application for them has been filed, i.e. WO 9740176. They bind to two or possibly three different regions (epitopes) on E2.

The role of E1 and E2 in the life cycle of the virus is not fully established, nor is the whole process of virus attachment and entry. Still, antibodies to the HVR of E2 can block infection in animals, and so can antibodies to other parts of HCV (most likely E2). Antibodies to E1 elicited by vaccination in chimpanzees correlated with reduced inflammation of the liver (despite constant viral levels in blood); the mechanism for this is unknown (Maertens et al., 2000).

There is currently no report within prior art on human monoclonal antibodies to the E1 protein derived from combinatorial libraries.

SUMMARY OF THE INVENTION

The present inventors have been able to generate human antibodies to the E1 protein. This was much more complicated than isolating antibodies against the E2 protein, as there seem to be an immuno-dominance in most infected individuals to generate anti-E2 antibodies rather than anti-E1 immunoglobulins. Initially, the inventors worked with a recombinant protein resembling the complexed E1/E2, the assumed native complex presented on the viral surface. Only anti-E2 antibodies could be isolated in those experiments. To solve the problem of generating anti-E1 antibodies, E1 was first cloned and expressed separately on the surface of eukaryotic cells. Subsequently, such E1 displaying cells were used for selection of anti-E1 binding clones from an antibody library displayed on filamentous phage, in order to avoid the immunodominant anti-E2 clones present in the phage antibody library.

In a first aspect, the invention provides a recombinant human monoclonal antibody, or antigen binding fragments thereof, that exhibits immunological binding affinity for a hepatitis C virus (HCV) E1 antigen, wherein said monoclonal antibody comprises an amino acid sequence homologous to the binding portion of a human antibody Fab molecule obtained from a combinatorial antibody library.

The monoclonal antibody according to the invention reacts with complexed HCV E1/E2 antigen. The monoclonal antibody according to the invention preferably reacts with genotypically different isolates of HCV virus. Furthermore, the monoclonal antibody according to the invention may be improved by mutation and new selection, i.e. so called affinity maturation in vitro, to increase the binding strength of the antibodies to E1.

The Fab molecule of the monoclonal antibody of the invention comprises the VH and VL domains respectively, of the heavy and light chains of the Fab molecule according to Seq. ID No. 1-56 of the enclosed Sequence Listning.

The monoclonal antibody according to the invention may be fused with a further substance for diagnostic or therapeutic purposes, for example a toxin, an antibody allowing targeting, e.g. against defense cells, a protein conferring modulated metabolism of the anti-E1 antibody, a marker for diagnosis, immunohistochemistry, imaging etc.

In a second aspect, the invention relates to a detecting immunological reagent comprising the monoclonal antibody according to the invention. For example, the reagent may be used in quantitative assays for detection and analysis of replication and assembly in the life cycle of the virus.

In a third aspect, the invention relates to an immunological assay comprising the above reagent. The assay may be a modified NOB assay as mentioned above. Alternatively, the immunoassay may be a qualitative assay to measure conformation of recombinant E1 in connection with the production of therapeutic and diagnostic agents.

In a fourth aspect, the invention relates to a drug or vaccine composition against HCV infection, comprising the monoclonal antibody according to the invention or any combination of antibodies, or antibody binding fragments, of the invention. The vaccine composition is formulated with pharmaceutically acceptable vehicles in a conventional manner and is intended for passive immunisation.

According to the present invention it is possible to produce human antibodies to parts of E2 (in particular the HVR region), and to the envelope protein, E1, in order to compose a "cocktail" of 3-6 or more human monoclonal antibodies. Such a mixture of antibodies to different proteins and protein regions of the virus has a much larger probability of severely affecting such a variable virus as HCV.

In a fifth aspect, the invention provides a method of treating a subject against HCV infection in a therapeutic or prophylactic purpose, comprising administration of the vaccine composition according to the invention to subjects in need thereof.

DETAILED DESCRIPTION OF THE INVENTION

Materials and Methods

Antibodies and Antisera

Monoclonal mouse anti-human-myc from Invitrogen was used in 1:150-1:75 dilution (9-19 µg/ml). Ascites produced mouse anti-E1 monoclonal antibody was diluted 1:250. A FITC conjugated rabbit-anti-mouse immunoglobulin from Dako was used as secondary antibody in 1:15-1:10 dilution (67-100 µg/ml).

Anti-HCV Phage Library Construction

The library was derived from a bone marrow donation from a patient infected with HCV genotype 1a. Construction of the library was performed as described in Allander et al, 2000. In brief, lymphocytes were isolated from bone marrow using Ficoll-Paque (Pharmacia), and total RNA was extracted by the acid guanidium thiocyanate-phenol method. First strand cDNA synthesis was performed using an oligo-dT primer and the "First strand cDNA synthesis" kit (Amersham Pharmacia). The cDNA was subsequently used as template for PCR amplification of γ1 Fd and κ light chains (Kang et al. 1991), and ligated into the phagemid vector pComb3H (Barbas and Wagner, 1995).

Construction of E1 Expression Vector

The signal sequence and echtodomain of E1 (aa 174 to 359) was inserted into the vector pDisplay (Invitrogen). The pDisplay vector has a mouse Igκ signal sequence upstream of its cloning cassette and a PDGF membrane anchor sequence downstream of the cassette for cell-surface expression. In addition, the vector contains two tag sequences so that the expressed protein will have a N-terminal Hemagglutinin A epitope tag, and a C-terminal myc epitope tag before the membrane anchor. The signal sequence and echtodomain fragment of E1 was PCR amplified from a full-length HCV clone (pcv H77c, genotype 1a), which was a generous gift from Dr J Bucht, NIH, USA (Yanagi et al., 1997). Since the hemagglutinin A tag would be localized N-terminal of the E1 fragment and possibly disturb recognition by anti-E1 or anti-myc antibodies, the signal sequence and the Hemagglutinin tag were deleted from the vector using Eco RI and Pst I (Life Technologies). The E1 fragment was subsequently inserted with the 3' end in the cloning cassette and the 5' end replacing the removed sequences. The PCR was performed as follows: first 94° C. 5 min; then 94° C. 1 min, 52° C. 0.5 min, and 72° C. 10 min for 35 cycles; and finally 72° C. 10 min. Primers (Symbion, Denmark) were designed to contain specific restriction enzyme sites for directional cloning and an ATG start codon in the sense primers: sense primer (H77C-S 1b) 5'-GG AAC CTT CCT GAA TTC GGC TTG GGG ATG TTC TCT ATC-3' (restriction site for Eco RI underlined), antisense primer (H77C-AS1) 5'-CAT GGA GAA ATA CGC CTG CAG CGC CAG-3' (restriction site for Pst I underlined). The PCR fragment was cleaved with the mentioned restriction endonucleases, and gel purified on 1% agarose. The band of correct size (approx. 600 bp) was cut out from the gel, and DNA was eluted using Concert DNA purification kit (Life Technologies). The pDisplay vector (Invitrogen) was cut using the same restriction enzymes and likewise gel purified. The fragment was ligated to the vector in 1:1, 1:3 and 1:6 ratios at +4° C. o.n. using T4 DNA ligase (Life Technologies). The 1:1 ligation product was linearized, self-religated and used to transform E. coli (XL-1 Blue, Stratagene) by electroporation. Single ampicillin resistant clones were picked and cultured, and DNA was extracted using Wizard® Plus Midipreps DNA purification system (Promega). To distinguish which clones contained correct insert, DNA from single clones was analyzed both by PCR and by restriction enzyme digestion.

Detection of E1 Expression on Eukaryotic Cells

Expression of the E1-myc construct was tested in CHO and HeLa cells. Cells were grown in 6-well plates to near confluence in RMPI 1640 (CHO cells) or DMEM (HeLa cells) supplemented with 10% fetal bovine serum (FBS) and 100 U/ml penicillin, streptomycin 100 µg/ml (Life Technologies). Transfection was performed using FuGENE 6 (Boehringer-Mannheim) with a FuGENE 6 to DNA ratio of 3-6 µl to 1-2 µg per well. Geneticin (Life Technologies) was added to the culture media, in a final concentration of 200 µg/ml, 48 h after transfection. Analysis with immunofluorescence microscope (Leitz DMRBE, Leica) and flowcytometry (FacSort, Becton Dickinson) were carried out on solubilized cells. Cells were loosened using a rubber policeman and washed twice in wash buffer Dulbeccos' PBS, 0.5% FBS, 0.1% sodium azide (Life Technologies, USA). Cells were centrifuged and resuspended in a small volume of primary antibody (anti-myc or anti-E1)

and incubated at RT for 60 min. After two to three washes in wash buffer, cells were incubated in the dark at RT for 30 min in secondary rabbit-anti-mouse Ig-FITC. Finally cells were briefly incubated in Hoerst 1:1000, washed 3 times and mounted on glass slides in 5-10 µl Vectashield(Vector). Cells to be analysed with flowcytometry were redisolved in 250 µl washbuffer.

Selection of Anti-E1 Clones

Anti-E1 clones were selected from three different sets of selections. For the first two sets, HeLa cells were grown to semi confluence in T75 culture flasks. In the first set of selections, cells were transfected with 8-9 µg E1 DNA (47-53 µl Fugene6). In the second set, HeLa cells were transfected twice with the E1 DNA to further increase the surface expression prior to selection. Cells were first transfected (5.5 µg DNA) in a T25 culture flask for two days, grown under Geneticin selection pressure for 5 days, and then moved and transfected in a T75 flask (16 µg DNA). In the third set, CHO cells were used because of their higher surface expression even after the first transfection. Cells were transfected with 16-30 µg DNA in T75 flasks. One to four days after transfection cells were harvested using a rubber policeman, and suspended in DPBS-4% nonfat milk-0.02% sodium azide. To deplete the phage library of non-specific binders, the phages were incubated with non-transfected cells for one hour on an orbit shaker 100 rpm at RT or incubated overnight at +4° C. and then on a turning-wheel (7 rpm) for one hour at RT. Cells were removed by centrifugation, and the depleted phages were incubated with transfected cells for 1.5-2 h on a turning-wheel at RT. Cells were then washed three times in washbuffer (Dulbeccos PBS, 0.5% FBS, 0.02% sodium azide). Cells were resuspended in 100 µl anti-myc 1:75 dilution and incubated at RT for 2 h. After two washes the cells were resuspended in FITC-anti-mouse-IgG 1:15 dilution and incubated in the dark for 1 h. The cells were washed twice before resuspended ($10^6$ cells/ml) in wash-buffer. Sorting was performed in a FACSVantage SE (Becton Dickinson). Phages were eluted from the sorted cells by adding 200 µl 0.1 M HCl-glycine pH 2.2. Eluted phages were used to infect freshly cultured XL-1 Blue. The infected bacteria were then plated out on LA-amp plates. The next day, colonies were harvested in SB and grown to a 50-100 ml culture. Phages were induced and harvested as described (Barbas el al., 1991), and used for a next round of selection.

Fab Expression and Initial Testing

Colonies were picked, propagated and analyzed as single clones. Fab production was induced and a periplasmic fraction was prepared by freeze thawing (Allander et al 2000). Fab production was determined in an ELISA using anti-Fd (The Binding Site, UK) and AP conjugated anti-Fab (PIERCE, USA). Specificity for the antigen was initially tested in an ELISA against an recombinant E1/E2 protein, or against recombinant E1 protein. The recombinant E1/E2 heterodimer protein (genotype 1a) expressed in CHO cells was generously provided by Dr M. Houghton, Chiron Corp. and has been described elsewhere (Spaete et al., 1992). The soluble E1 protein was expressed and secreted into the medium from COS cells, and was generously provided by Dr. A. Patel, MRC Virology Unit, Glasgow, U.K. The ELISA assays with these antigens were performed as described below.

ELISA Assay for Determination of Specific Binding of the Antibodies to HCV Proteins ELISA for E1 reactivity: GNA lectin (Sigma) was diluted to 2.5 µg/ml in PBS and coated to microtiter wells (Costar 3690) over night at room temperature. The wells were washed once in PBS with 0.05% Tween 20 (PBS-T) and the wells were blocked with 4% non-fat dry milk in PBS for 2 hours at room temperature. After discarding the blocking solution, 50 µl of recombinant E1 (approx. concentration 50 µg/ml) was added and incubated for two hours at room temperature. After the E1 solution had been discarded, the antibody preparations were added and bound antibodies detected as described below.

Recombinant E1/E2 heterodimer (genotype 1a) was diluted to 1 µg/ml in PBS, and coated to microtitre wells overnight at +4° C. Unbound antigen was discarded, and the wells were blocked with 5% non-fat dry milk in PBS for 60 minutes at room temperature. Blocking solution was discarded, and antibody solutions to be tested added in 1:3-1:24 dilutions (diluent: PBS with 0.05% Tween 20). The plates were incubated at 37° C. temperature for 2 hours, washed four times with PBS-T, and alkaline phosphatase (AP) coupled-goat anti-human F(ab')$_2$ (Pierce, Rocherford, Ill.) antibodies in a 1:1000 dilution were added. After 60 minutes at 37° and subsequent washes, substrate solution (p-nitrophenyl phosphate, Sigma, St. Louis, Mo.) was added and absorbency measured at 405 nm.

For control purposes, recombinant E2 (genotype 1a), or BSA (Sigma) coated at 1 µg/ml were used in corresponding ELISAs to control for unspecific reactivity.

Transfer of Fab Clones into IgG Format

The Fd and the light chain gene segments were transferred from the phagemide vector pComb3H to the eukaryotic vector pcIgG1 as previously reported (Samuelsson et al., 1996). Plasmid DNA was transfected into CHO cells using Lipofectamine Plus (Life Technologies) according to the manufacturer's instructions. Medium containing secreted IgG was harvested every second day and frozen until analyzed. The ELISA to determine IgG concentration used a rabbit anti-human IgG and an AP conjugated rabbit anti-human IgG, and a purified human IgG standard as reference (Dako) (Samuelsson et al., 1996).

Results

Library Size

Ligation of γ1 Fd genes into the pComb3H vector gave a library of $7.8 \times 10^6$ cfu/µg, and ligation of κ light chain genes into the pComb3H gave a library of $1.6 \times 10^7$ cfu/µg. The resulting combinatorial library comprised $3.7 \times 10^7$ members.

Construction of E1 Expression Vector

The first ligation of pDisplay vector and E1 fragment resulted in similar number of clones independent of ligation ratios. Plasmid DNA extracted from cultures of the 1:1 ligation was linearized and separated on a gel. Two bands of approximately 5.5 and 6.0 appeared on the gel. Since the expected correct sized band was 5.8 kb, both bands were purified and religated separately. Single clones were grown and insertion of the fragment was demonstrated by PCR using the same sense and antisense primers as in the cloning step; 9 clones out of 20 showed the correct fragment length. Subsequent restriction enzyme digestion showed that the correct sized fragment also could be cleaved from all 9 clones. Nucleic acid sequencing of the clones showed that they all differed from the original E1 sequence by a few nucleotides or more.

Assessment of E1 Expression on Eucaryotic Cells

Initially HeLa cells were preferred. To determine optimal expression of the myc-tag, expression was investigated by fluorescence microscopy and flow cytometry on day 1, 2, 4, and 7 after transfection. This time study indicated that immunofluorescence detection of the myc tag was optimal 4 days after transfection. For the second set of selection surface expression was increased slightly by transfecting the HeLa cells twice. For the third set CHO cells were chosen since they appear to be more tolerant to transfection as well as show clear E1 expression already after one day of transfection.

Selection of E1 Specific Clones

In the first round of each selection series, approximately $10^{11}$ cfu of phage library was depleted against $10^6$-$10^7$ non-transfected cells. Unbound, depleted phages were subsequently incubated with $3$-$8\times10^6$ transfected, E1 expressing cells. After sorting for myc positive cells, phages were eluted from the sorted cells and re-propagated in fresh XL1 blue. $2$-$8\times10^{10}$ to cfu of re-propagated phages were used in the next selection round.

In the first series, two rounds of selection were performed. After the second round, only 108 colonies were formed, 98 of which were tested in ELISAs for Fab expression and binding to recombinant E1/E2 antigen. Sixteen clones expressed Fab, of which nine were positive for binding to E1/E2. After nucleic acid sequencing, two clones were judged not to be proper Fab fragments. Two clones (clones 13 and 98) from this selection series were further characterised and included in the present collection of antibodies (Table 1, Seq ID No. 1-4).

In the second series, six selection rounds were performed. After the fourth round, 42 single clones were picked and assayed for Fab expression. Twentytwo clones produced Fab, while only two were positive when tested for E1 reactivity. Subsequent sequence analysis revealed that the clones were identical (clone 4:6; Seq ID No. 13-14). An additional clone, isolated from the sixth panning round in this series, was also characterised (clone 6a:5; Table 1 and Seq ID No. 15-16).

In the third series, two rounds of selection were made and the second round was repeated once. 45-75% of propagated clones expressed Fab. The majority of our E1 specific Fab clones were isolated from this selection series (clones with prefix 1:, 2a: and 2b:).

Reactivity to HCV Antigens

The reactivity of the different Fab clones to the HCV proteins E1, E1/E2 in complex, free E2 or BSA was determined by ELISA. All clones showed a significantly higher reactivity to E1 and/or E1/E2 than against E2 or BSA (negative control antigens) (Table 1). From these data, it seems that some clones may be particularly efficient binders: clones 1.4, 1:8, 2a:13, 2a:23, 2a:30, 2b:5 and 4:6

TABLE 1

Reactivity to HCV antigens and BSA by the Fab proteins (crude periplasmic preparations) as measured by ELISA ($OD_{405\,nm}$ values given).

| Fab clone | E1 | E1/E2 | E2 or BSA(B) | µg Fab/ml (approximative) |
|---|---|---|---|---|
| 13 | 0.20 | 0.16 | 0.03 (B) | >3 |
| 98 | 0.20 | 0.16 | 0.10 (B) | 5 |
| 1:4 | 0.78 | 0.67 | 0.27 (B) | 0.01 |
| 1:8 | 0.75 | 0.53 | 0.09 (B) | 0.01 |
| 1:9 | 0.96 | 0.67 | 0.16 (B) | 0.05 |
| 1:10 | 0.20 | 0.12 | 0.01 (B) | 0.01 |
| 4:6 | 0.97 | 0.20 | 0.03 | 0.24 |
| 6a:5 | 0.15 | 0.09 | 0.03 | 0.33 |
| 2a-2 | 1.00 | 0.32 | 0.18 | 0.64 |
| 2a-4 | 1.18 | 0.42 | 0.33 | 1.0 |
| 2a-5 | 0.89 | 0.08 | 0.07 | 0.44 |
| 2a-13 | 1.05 | 0.22 | 0.14 | 0.36 |
| 2a-14 | 0.36 | 0.09 | 0.07 | 0.72 |

TABLE 1-continued

Reactivity to HCV antigens and BSA by the Fab proteins (crude periplasmic preparations) as measured by ELISA ($OD_{405\,nm}$ values given).

| Fab clone | E1 | E1/E2 | E2 or BSA(B) | µg Fab/ml (approximative) |
|---|---|---|---|---|
| 2a-23 | 1.47 | 0.23 | 0.19 | 0.50 |
| 2a-25 | 1.46 | 0.33 | 0.24 | 0.11 |
| 2a-30 | 1.11 | 0.52 | 0.26 | 0.96 |
| 2a-32 | 0.61 | 0.09 | 0.07 | >1 |
| 2a-33 | 0.65 | 0.14 | 0.14 | >1 |
| 2a-37 | 0.99 | 0.48 | 0.29 (B) | 0.08 |
| 2a-40 | 1.21 | 0.17 | 0.17 | 1.0 |
| 2b-1 | 0.35 | 0.12 | 0.08 | 0.94 |
| 2b-3 | 1.18 | 0.19 | 0.12 | 1.0 |
| 2b-4 | 0.11 | 0.09 | 0.03 (B) | 0.68 |
| 2b-5 | 2.21 | 1.40 | 0.71 | >1.0 |
| 2b-7 | 0.47 | 0.32 | 0.18 | 0.54 |
| 2b-9 | 0.33 | 0.19 | 0.15 | 0.19 |
| 2b-10 | 0.48 | 0.11 | 0.13 | >1.0 |
| 2b-17 | 0.24 | nd | 0.05 | 0.16 |
| mouse mcl anti-E1 | >3.00 | >3.00 | 0.20 | |
| rabbit anti-E2 | nd | 0.15 | 0.72 | |
| PBS | 0.11 | 0.10 | 0.08 | |
| non-specific Fab | 0.20 | 0.11 | 0.14 (B) | |

For technical reasons, E2 was in some experiments replaced with BSA as negative control antigen (values marked with (B)).
nd = not determined

REFERENCES

Allander T, Drakenberg K, Beyene A, Rosa D, Abrignani S, Houghton M, Widell A, Grillner L, Persson MAA. Recombinant human monoclonal antibodies against different conformational epitopes of the E2 envelope glycoprotein of hepatitis C virus that inhibit its interactions with CD81. J Gen Virol 2000, 81: 2451-2459.

Barbas III CF, Kang A S, Lemer R A, Benkovic S J. Assembly of combinatorial antibody libraries on phage surfaces: the gene III site. Proc Natl Acad Sci USA 1991; 88: 7978-82.

Barbas III C F, Wagner J. Synthetic human antibodies: selecting and evolving functional proteins. Methods 1995; 8: 94-103.

Burioni R, Plaisant P, Manzin A, Rosa D, Delli Carri V, Bugli F, Solforosi L, Abrignani S, Varaldo P E, Fadda G, Clementi M. Dissection of human humoral immune response against hepatitis C virus E2 glycoprotein by repertoire cloning and generation of recombinant Fab fragments. Hepatology 1998; 28: 810-814.

Houghton M. Hepatitis C Virus. In Fields Virology, (eds B N Fields, D M Knipe, P M Howley) Lippincott-Raven Publishers, Philadelphia, 1996 pp 1035-1058.

Kang A S, Burton D R, Lemer R A. Combinatorial immunoglobulin libraries in phage λ. Methods: Comp. Methods in Enzymol. 1991; 2: 111-8.

Maertens G, Priem S, Ducatteeuw A, Verschoorl E, Verstrepen B, Roskams T, Desmet V, Fuller S, Van Hoek K, Vandeponseele P, Bosman F, Buyse M A, van Doorn L J, Heeney J, Kos A, Depla E. Improvement of chronic active hepatitis C in chronically infected chimpanzees after therapeutic vaccination With the HCV E1 protein. Acta Gastroenterologica Belgica. 2000; 63: 203.

Samuelsson A, Yari F, Hinkula J, Ersoy O, Norrby E, Persson MAA. Human antibodies from phage libraries: neutralizing activity against human immunodeficiency virus type 1 equally improved after expression as Fab and IgG in mammalian cells. Eur J Immunol 1996; 26: 3029-34.

Spaete R R, Alexander D, Rugroden M E, Choo Q L, Berger K, Crawford K, Kuo C, Leng S, Lee C, Ralston R, and others. Characterization of the hepatitis C virus E2/NS1 gene product expressed mammalian cells. Virology 1992; 188: 819-830.

Yanagi M, Purcell R H, Emerson S U, Bukh J. Transcripts from a single full-length cDNA clone of hepatitis C virus are infectious when directly transfected into the liver of a chimpanzee. Proc Natl Acad Sci USA 1997; 94:8738-8743.

The invention claimed is:

1. A human monoclonal antibody or antigen binding fragment thereof that exhibits immunological binding affinity for a hepatitis C virus (HCV) E1 antigen, said monoclonal antibody or antigen binding fragment thereof having a VH domain and a VL domain, wherein said VH domain comprises the amino acid sequence of SEQ ID NO: 43 and wherein said VL domain comprises the amino acid sequence of SEQ ID NO: 44.

2. A monoclonal antibody or antigen binding fragment thereof according to claim 1, wherein the monoclonal antibody or antigen binding fragment thereof reacts with complexed HCV E1/E2 antigen.

3. The monoclonal antibody or antigen binding fragment thereof according to claim 1 fused with a further substance for diagnostic or therapeutic purposes.

4. An immunological reagent comprising the monoclonal antibody or antigen binding fragment thereof according to claim 1.

* * * * *